(12) United States Patent
Riesenberger et al.

(10) Patent No.: US 10,729,889 B2
(45) Date of Patent: Aug. 4, 2020

(54) NEEDLE DEVICES WITH DUAL DIAMETER CANNULA AND RELATED METHODS

(71) Applicant: B. Braun Melsungen AG, Melsungen (DE)

(72) Inventors: Hermann Riesenberger, Bebra (DE); Mohamad Yasin bin Abdulla, Penang (MY)

(73) Assignee: B. Braun Melsungen AG, Melsungen (DE)

(*) Notice: Subject to any disclaimer, the term of this patent is extended or adjusted under 35 U.S.C. 154(b) by 147 days.

(21) Appl. No.: 14/940,622

(22) Filed: Nov. 13, 2015

(65) Prior Publication Data

US 2017/0136217 A1 May 18, 2017

(51) Int. Cl.
*A61M 25/06* (2006.01)
*A61M 25/00* (2006.01)
*A61M 39/12* (2006.01)
*A61M 39/24* (2006.01)

(52) U.S. Cl.
CPC .... *A61M 25/0618* (2013.01); *A61M 25/0097* (2013.01); *A61M 39/12* (2013.01); *A61M 39/24* (2013.01); *A61M 25/0606* (2013.01); *A61M 2207/00* (2013.01)

(58) Field of Classification Search
CPC ............ A61M 25/0618; A61M 25/0097
See application file for complete search history.

(56) References Cited

U.S. PATENT DOCUMENTS

| 4,383,530 A | 5/1983 | Bruno |
| 4,512,766 A | 4/1985 | Vailancourt |
| 4,735,614 A | 4/1988 | Yapp et al. |

(Continued)

FOREIGN PATENT DOCUMENTS

| EP | 0343438 | 11/1989 |
| EP | 0554841 A1 | 8/1993 |

(Continued)

OTHER PUBLICATIONS

International Search Report and Written Opinion on corresponding PCT application (PCT/EP2016/077390) from International Searching Authority (EPO) dated Feb. 6, 2017.

(Continued)

*Primary Examiner* — Rebecca E Eisenberg
*Assistant Examiner* — Tasnim Mehjabin Ahmed
(74) *Attorney, Agent, or Firm* — Klein, O'Neill & Singh, LLP (57) ABSTRACT

A needle device includes a catheter tube attached to a catheter hub, a needle attached to a needle hub, and a needle guard. The catheter hub has an interior cavity and a projection extending from an interior surface in the interior cavity. The needle projects through the catheter tube and has a needle tip extending out a distal end of the catheter tube in a ready position, a proximal end attached to a needle hub, and a shaft having a shaft diameter region, a reduced diameter region, and at least one transition region between the shaft diameter region and the reduced diameter region. The needle guard has a proximal wall and two arms extending distal the proximal wall. The two arms press against the shaft in the ready position and secure the needle tip in the protective position.

27 Claims, 4 Drawing Sheets

(56) References Cited

U.S. PATENT DOCUMENTS

| | | | |
|---|---|---|---|
| 4,781,691 A | 11/1988 | Gross | |
| 4,791,937 A | 12/1988 | Wang | |
| 4,917,668 A | 4/1990 | Haindl | |
| 4,966,587 A | 10/1990 | Baumgart | |
| 5,053,014 A | 10/1991 | Heugten | |
| 5,059,180 A | 10/1991 | McLees | |
| 5,085,648 A * | 2/1992 | Purdy | A61M 5/3273 604/198 |
| 5,135,504 A | 8/1992 | McLees | |
| 5,215,528 A | 6/1993 | Purdy et al. | |
| 5,558,651 A * | 9/1996 | Crawford | A61M 25/0618 604/110 |
| 5,810,780 A | 9/1998 | Brimhall et al. | |
| 5,885,252 A | 3/1999 | Liu | |
| 6,179,813 B1 | 1/2001 | Ballow et al. | |
| 6,287,278 B1 * | 9/2001 | Woehr | A61M 25/0618 604/110 |
| 6,443,929 B1 | 9/2002 | Kuracina et al. | |
| 6,551,284 B1 | 4/2003 | Greenberg et al. | |
| 6,616,630 B1 * | 9/2003 | Woehr | A61M 5/3273 604/110 |
| 6,623,458 B2 | 9/2003 | Woehr et al. | |
| 6,629,959 B2 | 10/2003 | Kuracina et al. | |
| 6,719,726 B2 | 4/2004 | Meng et al. | |
| 6,749,588 B1 | 6/2004 | Howell et al. | |
| D498,844 S | 11/2004 | Diamond et al. | |
| 6,860,871 B2 | 3/2005 | Kuracina et al. | |
| 7,214,211 B2 | 5/2007 | Woehr et al. | |
| 7,534,231 B2 | 5/2009 | Kuracina et al. | |
| 7,569,044 B2 | 8/2009 | Triplett et al. | |
| 7,670,317 B2 | 3/2010 | Cindrich et al. | |
| 7,691,088 B2 | 4/2010 | Howell | |
| 7,691,093 B2 | 4/2010 | Brimhall | |
| 7,722,567 B2 | 5/2010 | Tal | |
| 7,762,992 B2 | 7/2010 | Triplett et al. | |
| 7,798,994 B2 | 9/2010 | Brimhall | |
| 7,922,696 B2 | 4/2011 | Tal et al. | |
| 7,927,314 B2 | 4/2011 | Kuracina et al. | |
| 7,998,122 B2 | 8/2011 | Lynn et al. | |
| 8,038,666 B2 | 10/2011 | Triplett et al. | |
| 8,066,675 B2 | 11/2011 | Cindrich et al. | |
| 8,105,286 B2 | 1/2012 | Anderson et al. | |
| 8,202,251 B2 | 6/2012 | Bierman et al. | |
| 8,273,056 B2 * | 9/2012 | Kuracina | A61M 5/1626 604/110 |
| 8,333,735 B2 | 12/2012 | Woehr et al. | |
| 8,377,006 B2 | 2/2013 | Tal et al. | |
| 8,403,894 B2 | 3/2013 | Lynn et al. | |
| 8,414,539 B1 | 4/2013 | Kuracina et al. | |
| 8,444,605 B2 | 5/2013 | Kuracina et al. | |
| 8,475,416 B2 | 7/2013 | Lynn | |
| 8,491,527 B2 | 7/2013 | Triplett et al. | |
| 8,545,454 B2 | 10/2013 | Kuracina et al. | |
| 8,591,468 B2 | 11/2013 | Woehr et al. | |
| 8,652,104 B2 | 2/2014 | Goral et al. | |
| 8,672,888 B2 | 3/2014 | Tal | |
| 8,672,895 B2 | 3/2014 | Kuracina et al. | |
| 8,764,711 B2 | 7/2014 | Kuracina et al. | |
| 8,771,230 B2 | 7/2014 | White et al. | |
| 8,808,254 B2 | 8/2014 | Lynn | |
| 8,821,439 B2 | 9/2014 | Kuracina et al. | |
| 8,827,958 B2 | 9/2014 | Bierman et al. | |
| 8,900,192 B2 | 12/2014 | Anderson et al. | |
| 9,108,021 B2 | 8/2015 | Hyer et al. | |
| 9,138,252 B2 | 9/2015 | Bierman et al. | |
| 9,238,104 B2 | 1/2016 | Kuracina et al. | |
| 9,308,354 B2 | 4/2016 | Farrell et al. | |
| 9,399,116 B2 | 7/2016 | Goral et al. | |
| 9,399,119 B2 | 7/2016 | Kuracina et al. | |
| 9,440,052 B2 | 9/2016 | Kuracina et al. | |
| 9,545,495 B2 | 1/2017 | Goral et al. | |
| 9,610,403 B2 | 4/2017 | Kuracina et al. | |
| 9,657,790 B2 | 5/2017 | Sesser et al. | |
| 9,827,398 B2 | 11/2017 | White et al. | |
| 2010/0249707 A1 | 9/2010 | Woehr et al. | |
| 2012/0179104 A1 * | 7/2012 | Woehr | A61M 25/0618 604/164.08 |
| 2013/0023835 A1 | 1/2013 | Kuracina et al. | |

FOREIGN PATENT DOCUMENTS

| | | |
|---|---|---|
| EP | 0747084 | 12/1996 |
| EP | 0799626 | 10/1997 |
| WO | WO 99/08742 | 2/1999 |
| WO | WO 2007122958 A1 | 11/2007 |

OTHER PUBLICATIONS

International Preliminary Report on Patentability (Chapter I) on corresponding PCT application (PCT/EP2016/077390) from International Searching Authority (EPO) dated May 24, 2018.

Office Action on corresponding foreign application (EP Application No. 16798670.2) from the European Patent Office dated Sep. 30, 2019.

Written Opinion on corresponding foreign application (SG Application No. 11201803229T) from the Intellectual Property Office of Singapore dated Jul. 29, 2019.

* cited by examiner

NEEDLE DEVICES WITH DUAL DIAMETER CANNULA AND RELATED METHODS

FIELD OF ART

The disclosed invention generally relates to needle devices and more specifically to needles and needle guards that cover needle tips following activation to prevent inadvertent needle sticks.

BACKGROUND

Insertion procedure for an IV catheter assembly contains four basic steps: (1) the healthcare worker inserts the needle and catheter together into the patient's vein; (2) after insertion into the vein with the needle point, the catheter is forwarded into the vein of the patient by the healthcare worker pushing the catheter with his or her finger; (3) the healthcare worker withdraws the needle by grasping the hub end (opposite the point end) while at the same time applying pressure to the patient's skin at the insertion site with his or her free hand to slow down or stop the flow of blood through the catheter; and (4) the healthcare worker then tapes the exposed end of the catheter (the catheter hub) to the patient's skin and connects it to the source of the fluid to be administered into the patient's vein.

The problem is that immediately after the withdrawal of the needle from the patient's vein, the healthcare worker, who is at this time involved in at least two urgent procedures, must place the exposed needle tip at a nearby location and address the tasks required to accomplish the needle withdrawal. It is at this juncture that the exposed needle tip creates a danger of an accidental needle stick, which, under the circumstances, leaves the healthcare worker vulnerable to the transmission of various dangerous blood-borne pathogens, including AIDS and hepatitis.

Other needle types similarly expose healthcare workers to risks of accidental needle sticks. For example, a doctor administering an injection, using a straight needle, a Huber needle, an epidural needle, etc., may place the used needle on a tray for subsequent disposal by a nurse. During the period between placing the used needle on a tray or a work station to the time it is discarded, the used needle is a potential source for disease transmissions for those that work near or around the needle.

Accordingly, exposed needle tips should be covered immediately following use to ensure greater worker safety. Ideally, the procedure for covering the needle tip should be passive, self-activating, or at least simple to perform. In addition, the device for covering the needle should be reliable and robust.

Needle devices often include safety systems that cover the tip of the needle to prevent accidental sticks after placement of the catheter tube into the vasculature of a patient. These systems can be either passive or active. In some systems, the safety features are located inside the catheter hub in the ready position while in other systems they are external of the catheter hub. In either location, the safety features serve the same function, to cover the needle tip in order to prevent accidental needle sticks after venipuncture. Thus, great care must be exercised when installing the safety systems to prevent dimension changes or deformation which can hamper or hinder the function and performance of the safety systems.

SUMMARY

Aspects of the present disclosure include needle devices and related methods.

A further aspect of the present disclosure includes a needle device which can comprise a catheter tube attached to a catheter hub, said catheter hub comprising a hub body comprising an exterior surface and an interior surface defining an interior cavity, a projection extending from the interior surface in the interior cavity, a needle projecting through the catheter tube and having a needle tip extending distally of a distal end of the catheter tube in a ready to use position, a proximal end attached to a needle hub, and a shaft having a shaft diameter region, a reduced diameter region, and at least one transition region between the shaft diameter region and the reduced diameter region, and a needle guard comprising a proximal wall and two arms extending distal the proximal wall, the two arms pressing against the shaft in the ready position and securing the needle tip in the protective position.

The two arms can press against the reduced diameter region in the ready position.

Each arm of the needle guard can comprise a distal wall and an elbow section engaging the projection inside the interior cavity of the catheter hub in the ready position, aided by the reduced diameter region of the needle biasing the two arms outwardly.

A curved lip can extend from the distal walls and press against the reduced diameter region in the ready position.

The reduced diameter region can extend from the needle hub to the distal end of the catheter hub in the ready position.

A change in profile can be provided adjacent the needle tip, wherein the change in profile is larger than a perimeter defining an opening on the proximal wall.

The reduced diameter region can be centered about the distal walls in the ready position and the transition region can be located on opposite sides of the reduced diameter region.

A change in profile can be provided adjacent the needle tip, wherein the change in profile is larger than a perimeter defining an opening on the proximal wall.

The reduced diameter region can extend from the needle hub to adjacent the needle tip in the ready position.

The shaft diameter region can be larger than a perimeter defining an opening on the proximal wall.

An additional aspect of the present disclosure includes a method for manufacturing a needle device. The method can comprise attaching a catheter tube attached to a catheter hub, said catheter hub comprising a hub body comprising an exterior surface and an interior surface defining an interior cavity.

A still further aspect of the present disclosure includes a needle assembly, such as an over the needle catheter assembly, comprising a catheter hub and catheter tube with a distal end, a needle with a needle tip and a needle hub. The needle projects through the catheter hub and the catheter tube and the needle tip extends out the distal end of the catheter tube in a ready to use position.

The needle assembly can comprise a needle guard having a proximal wall with a proximally facing wall surface and a distally facing wall surface. The proximal wall can comprise a perimeter defining an opening for engaging a change in profile on the needle. Two arms can extend distally of the proximal wall.

The needle can comprise at least two different needle diameters and wherein the length of the needle with each of the two different diameters are longer than a typical change in profile or crimp. The diameters can be generally round. The reduced diameter can also have different cross-section shapes, such as oval, semi oval or elliptical having a horizontal width, or larger of two diameters, being about the same as the shaft diameter region and a vertical width, orthogonal to the horizontal width, being reduced from that of the shaft diameter region.

The two different diameters can include a shaft diameter region or section and a reduced diameter region or section. A transition region can connect the shaft diameter region and the reduced diameter region. The needle can further include a second transition region. The reduced diameter region can be located between the transition region and the second transition region.

The needle can further comprise a shaft diameter region located proximally of the second transition region.

For an embodiment with a single transition region, the length of the shaft diameter region can extend from the needle tip to just proximal of the distal end of the catheter tube up to about the location of the nose section of the catheter hub, where the catheter tube enters or exits the catheter hub.

Thus, an aspect of the present disclosure is understood to include a needle assembly comprising a cannula having at least two different diameters and wherein the larger of the two diameters has a length that extend from the needle tip to a position proximal of the distal opening of the catheter tube and up to about a location of a nose section of a catheter hub, where the catheter tube enters or exits the catheter hub. The larger of the two diameters can be called a shaft diameter region and the smaller of the two diameters can be called a reduced diameter region.

A needle guard can be seated inside the interior of the catheter hub and wherein one or two arms of the needle guard, such as end walls or distal walls with optional curved lips, are biased outwardly by the reduced diameter region into engagement with the catheter hub. For example, the arms can have elbows or elbow sections and wherein contact by the two distal walls or curved lips force the elbows radially outwardly into engagement with the catheter hub so that at least one of the two elbows or elbow sections can engage an internal projection inside the catheter hub.

Advantageously, the needle with at least two different diameters can be sized with a catheter tube that fits around the larger of the two diameters to allow for greater infusion rate compared to when the catheter tube is sized to fit around the smaller of the two diameters. The larger of the two diameters can be called a shaft diameter region and the smaller of the two diameters can be called a reduced diameter region. Further, because a needle guard with one or two arms can be biased by the reduced diameter region, the amount of bias, measured in distance, on the one or two arms is less than when the one or two arms are biased by the shaft diameter region, such as when a single diameter needle with the same diameter as the shaft diameter region biasing the one or two arms. This can translate to less distortion on the one or two arms for a given interior cavity space, such as for an interior cavity with a Luer taper.

The method can further comprise projecting a needle through the catheter tube so that a needle tip of the needle extends distally of a distal end of the catheter tube in a ready to use position, said needle having a proximal end attached to a needle hub and a shaft having a shaft diameter region, a reduced diameter region, and at least one transition region between the shaft diameter region and the reduced diameter region.

The method can further comprise providing a needle guard comprising a proximal wall and two arms extending distal the proximal wall, the two arms pressing against the shaft in the ready position and securing the needle tip in the protective position.

The method can further comprise pressing the two arms against the reduced diameter region in the ready position.

The method can further comprise engaging an elbow section of each arm against the projection inside the interior cavity of the catheter hub in the ready position, aided by the reduced diameter region of the needle biasing the two arms outwardly.

A curved lip can extend from a distal walls of each arm presses against the reduced diameter region in the ready position.

The reduced diameter region can extend from the needle hub to the distal end of the catheter hub in the ready position.

A change in profile can be provided adjacent the needle tip, wherein the change in profile is larger than a perimeter defining an opening on the proximal wall.

The reduced diameter region can be centered about the distal walls in the ready position and the transition region is located on opposite sides of the reduced diameter region.

A change in profile can be provided adjacent the needle tip, wherein the change in profile is larger than a perimeter defining an opening on the proximal wall.

The reduced diameter region can extend from the needle hub to adjacent the needle tip in the ready position.

The shaft diameter region can be larger than a perimeter defining an opening on the proximal wall.

The method or apparatus can further include one or more structural features and/or steps described herein.

Another aspect of the present disclosure includes a needle device comprising a catheter hub having a body defining an interior cavity and having a proximal opening, a catheter tube extending distally of the catheter hub and comprising a distal opening, a needle hub, a needle extending distally of the needle hub, said needle comprising a shaft and a needle tip extending distally of the distal opening of the catheter tube in a ready to use position, said needle having a shaft diameter region and a reduced diameter region connected to one another by a transition region, an outer diameter of the needle at the shaft diameter region is larger than an outer diameter of the needle at the reduced diameter region, and at least part of the shaft diameter region and the transition region are located in a bore of the catheter tube, proximal of the distal opening, and a needle guard comprising a proximal wall and at least one arm extending distal the proximal wall, the at least one arm pressing against the reduced diameter region in the ready position and securing the needle tip in a protective position.

The needle guard can have two arms pressing against the reduced diameter region in the ready position.

The two arms of the needle guard each comprises a distal wall and an elbow section and at least one of the elbow sections engaging a projection extending from an interior surface of the interior cavity in the ready position, the reduced diameter region of the needle biasing the two arms outwardly.

A curved lip can extend from each distal wall and press against the reduced diameter region in the ready position.

The reduced diameter region can extend from the needle hub to the distal end of the catheter hub in the ready position.

The needle can further comprise a change in profile adjacent the needle tip, wherein the change in profile is larger than a perimeter defining an opening on the proximal wall.

The needle can further comprise a shaft diameter region proximal of the reduced diameter region.

The needle further comprises a change in profile adjacent the needle tip, wherein the change in profile is larger than a perimeter defining an opening on the proximal wall.

The reduced diameter region can extend from the needle hub to adjacent the needle tip in the ready position.

The shaft diameter region can be larger than a perimeter defining an opening on the proximal wall.

Another aspect of the present disclosure includes a method for manufacturing a needle device, the method comprising: attaching a catheter tube to a catheter hub, said catheter hub comprising a hub body comprising an exterior surface and an interior surface defining an interior cavity, projecting a needle through the catheter tube so that a needle tip of the needle extends distally of a distal end of the catheter tube in a ready to use position, said needle having a proximal end attached to a needle hub and a shaft having a shaft diameter region, a reduced diameter region, and a transition region between the shaft diameter region and the reduced diameter region; and providing a needle guard comprising a proximal wall and two arms extending distally of the proximal wall, the two arms pressing against the reduced diameter region in the ready position; and wherein the shaft diameter region has an outside diameter that is larger than an outside diameter of the reduced diameter region and wherein at least part of the shaft diameter region and the transition region are located in a bore of the catheter tube proximal of the distal end of the catheter tube in the ready to use position.

The method can further comprise pressing the two arms against the reduced diameter region in the ready position.

The method can further comprise engaging an elbow section of at least one of the arms against the projection inside the interior cavity of the catheter hub in the ready position and the two arms being biased outwardly by the reduced diameter region of the needle.

A curved lip can extend from a distal wall of each arm and press against the reduced diameter region in the ready position.

The reduced diameter region can extend from the needle hub to the distal end of the catheter hub in the ready position.

The needle can further comprise a change in profile adjacent the needle tip, wherein the change in profile is larger than a perimeter defining an opening on the proximal wall.

The reduced diameter region can be centered about the distal walls in the ready position and the transition region is located on opposite sides of the reduced diameter region.

The needle can further comprise a change in profile adjacent the needle tip, wherein the change in profile is larger than a perimeter defining an opening on the proximal wall.

The reduced diameter region extends from the needle hub to adjacent the needle tip in the ready position.

The shaft diameter region can be larger than a perimeter defining an opening on the proximal wall.

Another aspect of the present disclosure can include a needle device comprising: a needle having a proximal end attached to a needle hub, a needle tip at a distal end, a reduced diameter region located proximal of the needle tip and proximally of a shaft diameter region, which has a larger outside dimension than an outside diameter dimension of the reduced diameter region, and a change in profile; and a needle guard comprising a proximal wall having a proximally facing wall surface and a distally facing wall surface, two arms extending distally of the distally facing wall surface, and wherein the two arm press against the reduced diameter region.

BRIEF DESCRIPTION OF THE DRAWINGS

These and other features and advantages of the present devices, systems, and methods will become appreciated as the same becomes better understood with reference to the specification, claims and appended drawings wherein:

DETAILED DESCRIPTION

The detailed description set forth below in connection with the appended drawings is intended as a description of the presently preferred embodiments of needle devices provided in accordance with aspects of the present assemblies, systems, and methods and is not intended to represent the only forms in which the present devices, systems, and methods may be constructed or utilized. The description sets forth the features and the steps for constructing and using the embodiments of the present assemblies, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Figure 1A:
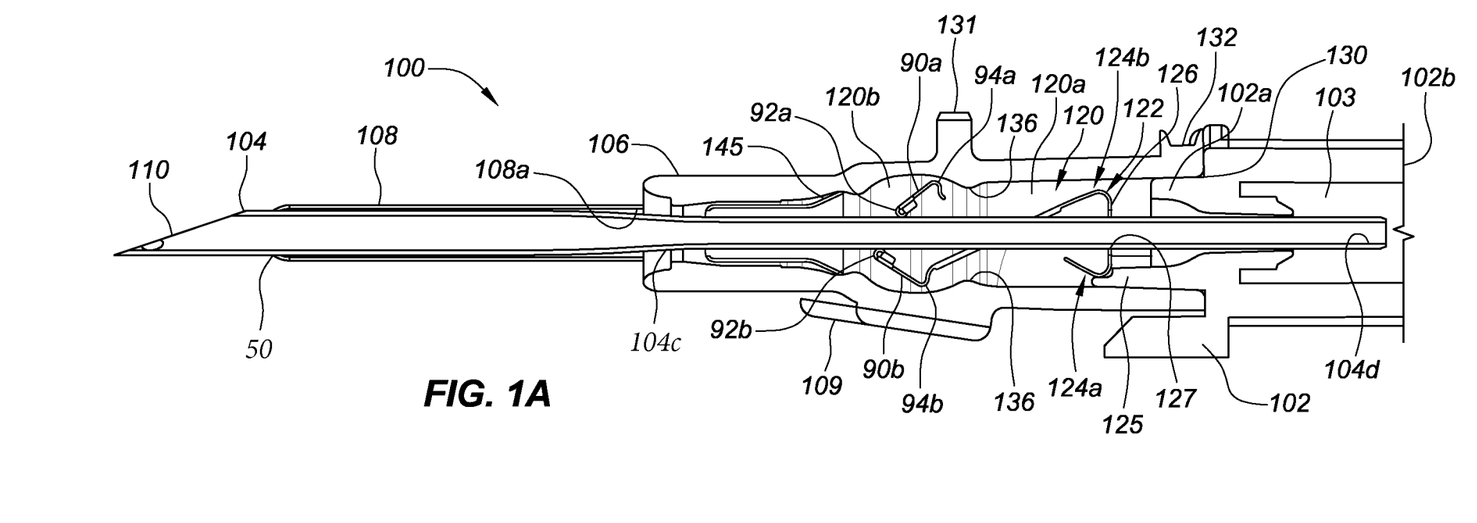
FIG. 1A is a cross-sectional side view of a needle device in accordance with aspects of the present disclosure in a ready position.

With reference now to FIG. 1A, a cross-sectional side view of an embodiment of a needle device 100, such as an over-the-needle catheter assembly or an IV catheter assembly, provided in accordance with aspects of the present disclosure is shown. FIG. 1A shows the needle device 100 in an installed or ready to use position in which the needle tip extends distally of a distal end 50 of the catheter tube for accessing the vasculature of a patient. In an example, the needle device 100 comprises a catheter hub 106 having a catheter hub body with a proximal end 130, an interior cavity 120, a catheter tube 108 extending distally from a distal end of the catheter hub 106, a needle hub 102 attached to the proximal end 130, a cannula or needle 104 extending distally of the needle hub 102 and projecting through the proximal end 130 and the catheter tube 108 and having the needle tip 110 extending distally of a distal opening of the catheter tube. A needle guard 122 is slidably positioned on the needle 104 and is located in the interior cavity 120 of the catheter hub. A proximal end of the catheter tube 108 can attach to the catheter hub 106 using a bushing 145 or other conventional means.

The proximal end 130 of the catheter hub 106 has a female Luer taper with external threads 132, also known as a threaded female Luer connector. The female Luer connector is configured to matingly receive a male Luer connector, such as an IV line, a Luer access connector, a syringe tip, a vent plug, an IV set, an extension set, another known connector, or future-developed IV devices with a Luer tip. Each of these components can be sized and configured in conformity with at least some of the International Standards Organization (ISO) standards for female and male Luer connections under current or future standards. For discussion purposes, any one of these components or the class of these components can be referred to as a male medical implement or a male connector. As shown, the threaded female Luer connector receives a nose section 102a of the needle hub 102. A physical abutment is provided between the catheter hub and the needle hub so as to set the distance the needle tip extends out the distal end 50 of the catheter tube.

The interior cavity 120 of the catheter hub 106 can be divided into an open chamber 120a and a holding chamber 120b distal of the open chamber 120a. The open chamber 120a is separated from the holding chamber 120b by a change in profile 136 inside the interior cavity 120. The change in profile 136 can be defined by a first interior diameter located next to a larger second interior diameter. The smaller diameter can be viewed as a projection and therefore the change in profile 136 can be called a projection 136, or an interior projection, which can be configured for retaining the needle guard 122 in the ready position, as shown in FIGS. 1A, 1C, 2A, and 3A. The projection 136 can also be used for retaining the needle guard 122 during retraction of the needle 104 following successful venipuncture.

As shown, the change in profile 136 can embody a single continuous protrusion formed around a periphery or interior diameter of the interior cavity 120. The projection 136 can have two surfaces having an apex and wherein the two surfaces can include a taper towards the open chamber 120a and taper towards the holding chamber 120b on the other side of the apex. However, the two tapered surfaces do not need to be symmetrical to still practice the present needle device. The tapered portions of the projection 136 can be selected to interact with the needle guard 122 so that the latter can be installed easily in the ready position and be readily removable during needle 104 withdrawal, as further discussed in detail below. In another example, the projection 136 can comprise two or more spaced apart sections formed around a periphery of the interior cavity 120 instead of a continuous annular ring.

The catheter hub 106 can include a tab 131 on an exterior thereof configured for use as leverage when handling the device 100, such as to push against during insertion or removal of the needle 104. A pair of wings 109 may extend laterally of the catheter hub 106 to support and stabilize the catheter hub 106 against the patient following successful venipuncture. Optionally, the tab 131 and the wings 109 can be omitted.

In the ready position, the needle 104 projects distally from a nose section 102a of the needle hub 102 through the catheter hub 106. The needle 104 has a needle tip 110 extending out a distal end of the catheter tube 108, as previously described. A proximal end of the needle 104 can extend into a flashback chamber 103 of the needle hub 102, which has an opening at a proximal end 102b that can be closed by a vent plug (not shown). Optionally, the vent plug can have sampling features that allow blood to be collected and dispensed, such as on a glucose strip or a Petri disc. An exemplary blood stopper can be similar to the blood stopper disclosed in pending U.S. patent application Ser. No. 14/576,802, filed Dec. 19, 2014, the contents of which are expressly incorporated herein by reference.

The needle tip 110 is configured for penetrating the epidermal layer of a patient and accessing the vasculature of the patient. The needle hub 102 can have a needle guard extension 125 extending from the nose section 102a into the open chamber 120a of the interior cavity 120 for pushing the needle guard 122 into the interior cavity 120b during assembly, the details of which will be further explained below.

As shown in FIG. 1A, the needle guard 122 is positioned completely inside the interior cavity 120 of the catheter hub 106 in the ready position. In other examples, the needle guard 122 can be positioned partially inside the catheter hub body 106 or completely outside the catheter hub 106, such as in a shroud or a separate needle guard housing between the catheter hub 106 and the needle hub 102. An exemplary needle guard located in a needle guard housing is disclosed in U.S. Pat. No. 8,460,247, the contents of which are expressly incorporated herein by reference. The needle guard 122 may be similar to the needle guards 122 disclosed in U.S. Pat. No. 6,616,630. As shown in FIG. 1A, the needle guard 122 can have a proximal wall 126 and two arms 124a, 124b extending distally of the proximal wall 126. Each arm 124a, 124b can include an extending portion 93a, 93b extending from the proximal wall 126, a distal wall 90a, 90b for blocking the needle tip 110 in a protective position (as shown in FIG. 1D), and an elbow section 94a, 94b coupling the distal wall 90a, 90b to the extending portion 93a, 93b.

The proximal wall 126 can comprise a perimeter defining a proximal opening 127 having the needle 104 passing therethrough. The proximal wall 126 can have a proximally facing wall surface and a distally facing wall surface and a perimeter defining an opening formed through the proximal wall, through the proximally facing wall surface and distally facing wall surface. The proximal opening 127 is configured for engaging a change in profile 128 of the needle 104 following placement of the catheter tube 108 into a patient's vasculature. The change in profile can be a crimp, a bulge, a sleeve, or a material buildup formed on the needle shaft adjacent the needle tip 110 to prevent the needle guard 122 from displacing distally off of the needle 104 in the protective position.

A curved lip 92a, 92b may be incorporated at each end of the distal wall 90a, 90b opposite the elbow section 94a, 94b. When incorporated, the curved lips 92a, 92b can reduce friction between the distal walls 90a, 90b and the needle shaft of the needle 104 as the needle 104 slides relative to the needle guard 122 through the opening 127. In other examples, the distal walls 90a, 90b can simply terminate in a straight edge.

Figure 1B:
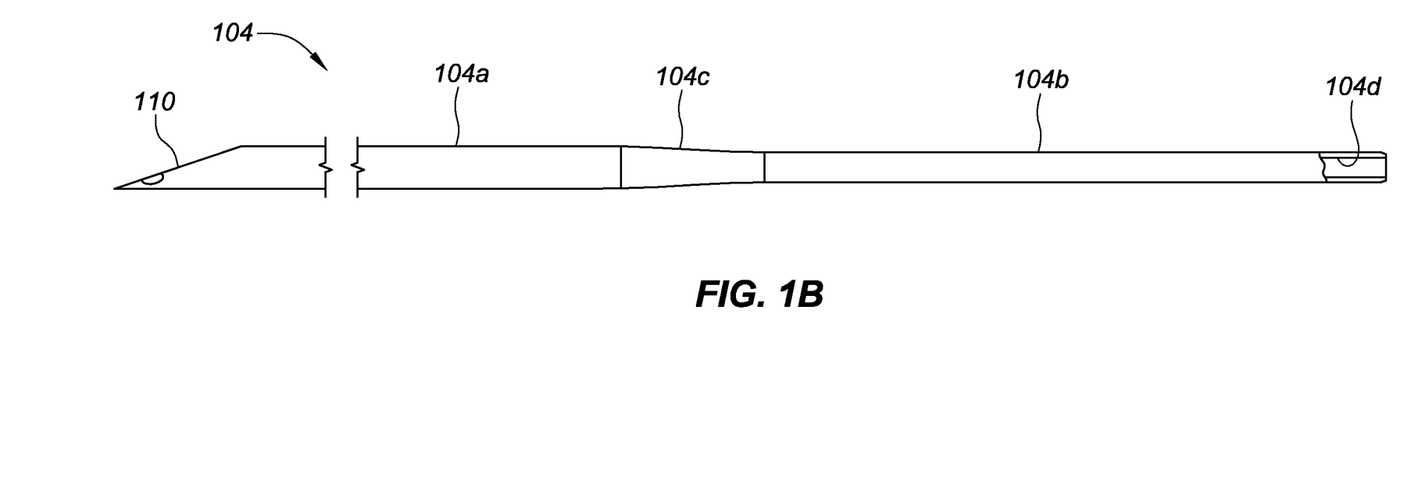
FIG. 1B is a side view of the needle in the needle device of FIG. 1A.
Figure 1C:
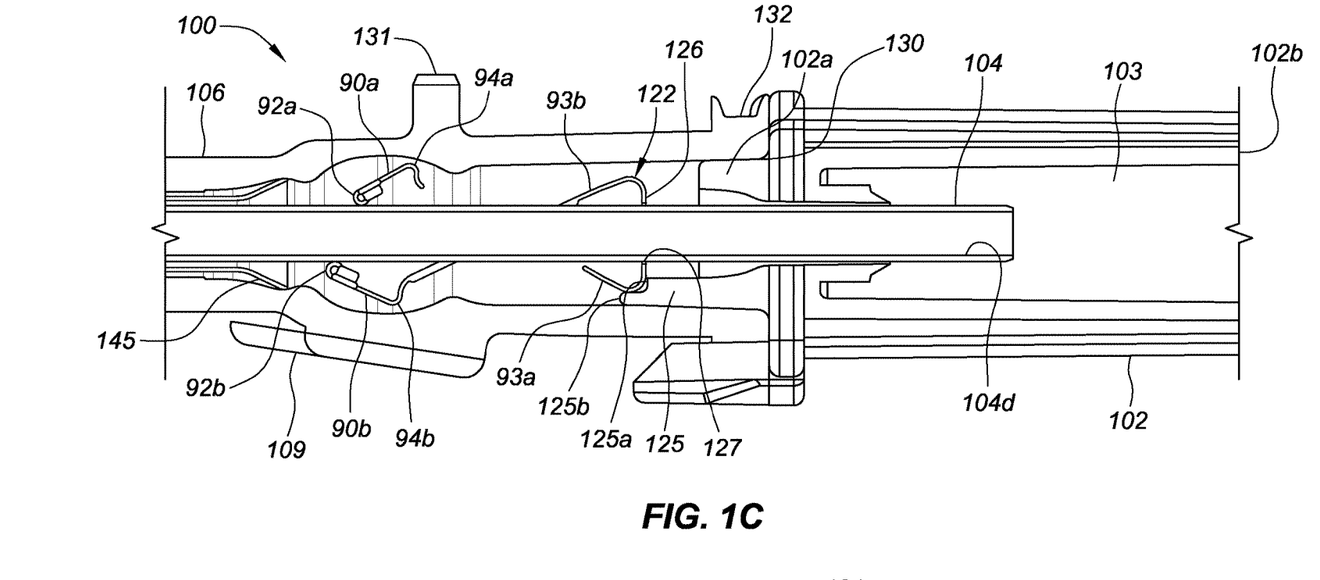
FIG. 1C is a close-up view of the needle device of FIG. 1A.
Figure 1D:
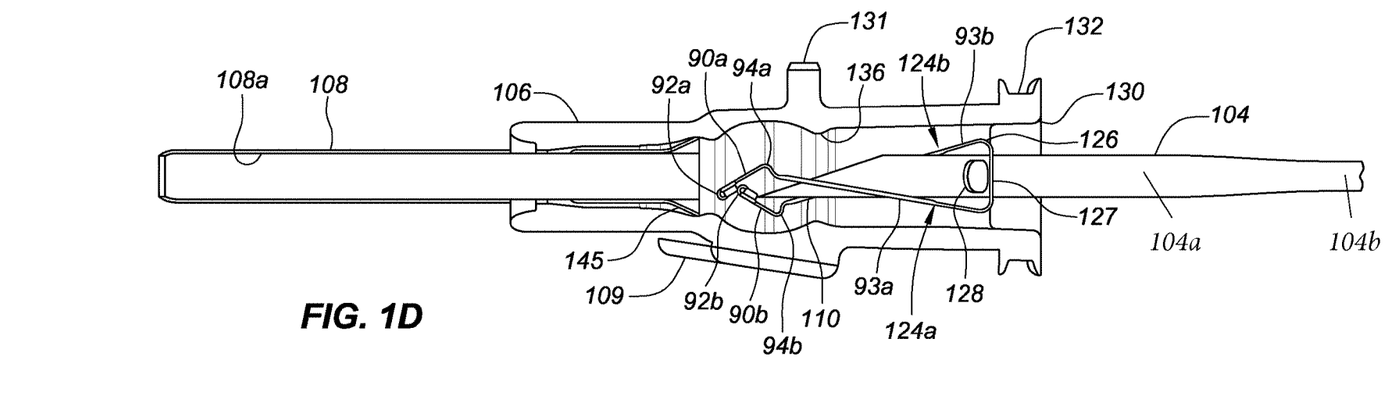
FIG. 1D is a cross-sectional side view of the needle device of FIG. 1A with the needle secured in a protective position.

The extending portions 93a, 93b can intersect one another when viewed along the side view of FIG. 1A in both the ready position and in the protective position (FIG. 1D). In other examples, the two arms 124a, 124b extend axially of the proximal wall 126 and do not intersect one another in the ready to use position. In still other examples, only a single arm 124a is incorporated with the needle guard. The needle 104 biases the two arms 124a, 124b outwardly so that the cross-sectional dimension measured at the radial outer ends of the two elbow sections 94a, 94b is larger than the dimension of the projection 136 inside the interior cavity of the catheter hub 106 in the ready position. This prevents the needle guard from being pulled in the proximal direction until after the two elbow sections are allowed to collapse or reduce in dimension to pass through the projection 136 when pulled in the proximal direction.

As shown, the distal walls 90a, 90b are maintained inside the holding chamber 120b with the elbow sections 94a, 94b engaging the projection 136 to prevent the needle guard 122 from moving proximally out of the holding chamber 102b while in the ready position and during needle 104 removal as will be discussed in detail below. In some examples, only one of the elbow sections 94a, 94b can engage the projection. The two elbow sections can be offset in the axial direction. Physical characteristics of the needle 104 in the needle device of FIG. 1A are illustrated more clearly in FIG. 1B.

Referring now to FIG. 1B, the shaft of the needle 104 is shown with a nearly constant outer diameter from just proximal of the bevel section of the needle tip 110 to a certain distance proximal of the needle tip 110 and proximal of the distal end 50 of the catheter tube, at which point the outer diameter reduces to a smaller outer diameter than the diameter of the needle shaft near the needle tip. Thus, the needle 104 can have a continuous shaft with two different diameters. The term diameter as used herein is understood to mean outside diameter of the needle. The needle shaft with different diameters of the present disclosure are distinguishable from a crimp or a change in profile on a single diameter shaft, which is limited to a single distinct section of a single diameter shaft and wherein the dimensions of the single diameter shaft is generally the same distal and proximal of the crimp or change in profile. Further, a crimp usually comprises an enlarged portion along one plane and a recessed portion along another plane.

As shown in FIG. 1D, the present needle shaft comprises a change in profile 128 and two different diameter regions including a shaft diameter region 104a and a reduced diameter region 104b and wherein the change in profile 128 is formed at the shaft diameter region 104a, which has a larger outside diameter than the reduced diameter region 104b.

For discussion purposes, the larger of the two diameters may be called a first diameter region or a shaft diameter region 104a and the smaller of the two diameters may be called a second diameter region or a reduced diameter region 104b. The different regions may also be referred to as sections.

The shaft diameter region 104a can be formed using conventional extrusion or fabrication methods to form the needle to a first diameter or original extruded diameter and the reduced diameter region 104b can be formed by further swaging, squeezing, or extruding the shaft to a smaller diameter. In other examples, the shaft diameter region 104a and the reduced diameter region 104b are first formed as two separate needle sections having different outer diameters that are then attached together, such as by welding, to form the needle 104. A transition section, such as a reducer or an enlarger can be placed between the two different diameter sections.

As shown, the outer diameter of the shaft diameter region 104a begins to taper towards the reduced diameter region 104b a certain distance proximal of the needle tip 110 and proximal of the distal end of the catheter tube. The tapered region may be referred to as a transition region 104c. Thus, the shaft of the needle 104 in FIG. 1B can have at least three regions or sections: (1) the shaft diameter region 104a; (2) the reduced diameter region 104b, which has a smaller outer diameter than the shaft diameter region 104a; and (3) a transition region 104c located between the shaft diameter region 104a and the reduced diameter region 104b.

In an example, the shaft diameter region 104a extends from the needle tip 110 to the transition region 104c. The diameter of the shaft diameter region 104a may be sized depending on the depth and the type of tissue the needle 104 is intended to penetrate. The diameter of the shaft diameter region 104a can also be selected depending on the infusion rate to be dispensed and therefore the catheter tube size for use with the shaft diameter region. For example, a 14 gauge needle selected for the shaft diameter region 104a will allow for use of the needle 104 with a relatively larger catheter tube 108, which then allows for a relatively greater infusion rate, than for a 16 gauge or a 18 gauge needle.

Thus, an aspect of the present disclosure is a catheter assembly comprising a catheter tube positioned around or over a needle shaft and wherein the needle shaft has at least two different shaft diameters and wherein the bore of the catheter tube is sized and shaped to fit over the larger of the two diameters. The bore of the catheter tube can also be sized and shaped to fit over both diameter regions of the needle shaft. For example, the needle can have two different diameter sections or regions, as discussed herein, and wherein at least part of both diameter regions are located inside the bore of the catheter tube distal of the nose section of the catheter hub and the larger of the two diameters located proximal of the distal opening of the catheter tube.

The distal end 50 of the catheter tube 108 can neck or taper down to form a seal with the larger of the two diameters 104a near the needle tip 110. Further, because the transition region 104c and possibly part of the needle shaft with the smaller of the two diameters, such as the reduced diameter region 104b, are located inside the bore of the catheter tube, the present needle assembly has at least two different annular spaces. For example, the annular space between the needle and the catheter tube at the shaft diameter region 104a, proximal of the tapered distal end 50, will be smaller or narrower than the annular space between the needle and the catheter tube at the reduced diameter region 104b. For clarity, the catheter tube is understood to have a generally constant outside diameter and inside diameter, excluding the reduced distal end 50 and the pinched proximal end for securing the catheter tube to the catheter hub.

An aspect of the present disclosure is further understood to include a variable annular space region at the transition region 104c of the needle shaft. For example, as the transition region 104c tapers from the shaft diameter region 104a to the reduced diameter region 104b, the annular space at the transition region 104c is variable at least along part of the length of the transition region 104c.

In the ready position, the distal end 50 of the catheter tube 108 can taper inwardly to form a seal against the shaft diameter region 104a and to facilitate insertion of the combination needle and catheter tube into the patient. The shaft diameter region 104a extends from the needle tip 110 to at least just proximal of the tapered distal end 50 of the catheter tube 108 so that at least some of the shaft diameter region 104a is located proximally of the tapered distal end 50 and forms an annular space with an interior 108a of the catheter tube.

In some examples, the length of the shaft diameter region 104a that is located proximally of the distal end 50, which can be called a shaft diameter region recessed length, is at least 0.1 times the length of the shaft diameter region 104a that is located distally of the distal end 50 of the catheter tube. In some examples, the shaft diameter region recessed length is about 0.5 times up to about 80% of the total length of the needle shaft. Thus, if the shaft diameter region recessed length is relatively short, such as being only one time that of the portion that extends distally of the distal end 50, then the remaining portions of the needle located inside the bore of the catheter tube will comprise the transition region 104c and the reduced diameter region 104b.

In a particular example, the shaft diameter region recessed length is about three times the length that is located distally of the distal end 50 of the catheter tube to about ten times the length that is located distally of the distal end 50 of the catheter tube. This configuration in which the shaft diameter region recessed length is located proximally of the reduced distal end 50 of the catheter tube allows the needle to support the distal end and distal section of the catheter tube during catherization, allows the catheter tube to increase in size to accommodate the relatively larger diameter section, i.e., the shaft diameter region 104a, and to have a reduced diameter region 104b at the proximal end for use with a needle guard so that the two arms of the needle guard are not biased outwardly by the needle the same amount as when the entire length of the needle has the same diameter as the shaft diameter region 104a. Further, because the catheter tube size is increased in size to accommodate the larger of at least two cannula diameters, greater infusion flow rate can be pushed through the catheter tube than a comparable catheter tube for just the reduced diameter region 104b.

Referring back again to FIG. 1A, the transition region 104c is shown located at or near the distal end of the catheter hub 106 and has a tapered section that tapers inwardly towards the reduced diameter region 104b. The transition region 104c may taper gradually or abruptly from the shaft diameter region 104a to the reduced diameter region 104b. In other words, the length of the transition region can vary with a longer length for producing a gradual taper and a shorter length for producing a relatively steeper taper. Alternatively, a step may be incorporated instead of the transition region 104c to connect the shaft diameter region 104a to the reduced diameter region 104b. As the step, which can be more akin to an abrupt reducer, transitions the large diameter region to the smaller diameter region, it can also be considered a transition region.

Typically, the more gradual the taper is the less the frictional loss is through the bore 104d of the needle 104 at the transition. A step transition will have a higher frictional loss than a gradual taper transition. The reduced diameter region 104b is not expected to lead to a measurably slow blood flashback following successful venipuncture. Thus, the primary flashback time using a dual diameter cannula of the present disclosure is not noticeably affected. Exteriorly, the more gradual the taper is the less friction and resistance will be when the arms 124a, 124b of the needle guard, such as the distal ends of the needle guard, contact the cannula during retraction of the cannula for smooth withdrawal.

The reduced diameter region 104b can extend from the transition region 104c to the proximal end of the needle 104. The taper of the transition region 104c and the diameter of the reduced diameter region 104b can be produced by mechanical swaging or controlled squeezing of a drawn cannula before or after the needle tip 110 is formed.

In some examples, a second transition region proximal of the transition region 104c is incorporated to produce a second reduced diameter region proximal of the reduced diameter region 104b. The end of the second reduced diameter region in the present alternative embodiment can attach to the needle hub. For example, a needle in accordance to aspects of the present disclosure can include a first large diameter section having a 14 gauge needle section at the needle tip, a transition section, a 16 gauge needle section, a second transition section, and a 18 gauge needle section at the proximal end of the needle shaft that attaches to the needle hub.

FIG. 1C shows a close-up view of the needle guard 122 in the catheter hub 106 in the ready position with the curved lips 92a, 92b of the two distal walls 90a, 90b pressed against the reduced diameter region 104b of the needle in the ready position. When assembling the needle device 100, the needle guard 122 can be slidably positioned on the needle 104 proximal of the needle tip 110 and proximal of the change in profile 128. The needle proximal end 104d is then placed in through the needle holding bore of the needle hub and secured thereto, such as by an adhesive. The proximal wall 126 of the needle guard 122 can either be positioned in contact with the needle guard extension 125 on the needle hub or be positioned distal or spaced from the needle guard extension 125.

The proximal wall 126 can abut a seating surface 125a of the needle guard extension 125 and align with a vertical support wall 125b parallel to the axis of the needle 104. The curved lips 92a, 92b or distal walls 90a, 90b if no curved lips are incorporated are in contact with the reduced diameter region 104b. Said differently, the reduced diameter region 104b of the shaft biases the elbow sections 94a, 94b outwardly when the two curved lips or two distal walls contact the sides of the needle. When the two distal walls or curved lips are not in contact with the side of the needle, the elbow sections are allowed to collapse or decrease in cross-sectional dimension, as shown in FIG. 1D. Where the needle guard 122 is spaced from the needle guard extension 125 during installation, the proximal wall 126 is distal of the needle guard extension 125 with the curved lips 92a, 92b or distal walls 90a, 90b pressing against the shaft diameter region 104a, the transition region 104c, or the reduced diameter region 104b, depending where along the axial length of the needle the needle guard is initially positioned.

With the needle guard 122 positioned on the needle 104 and the elbow sections 94a, 94b biased outwardly by the needle 104, the needle 104 with the needle hub 102 can be inserted distally into the catheter hub 106 through the proximal opening 130 and into the interior cavity 120. During insertion of the needle 104, the elbow sections 94a, 94b eventually encounter the projection 136, which can prevent the needle guard 122 from moving further distally into the holding chamber 120b unless the two elbow sections are compressed and/or deflected. At this juncture, the needle 104 can still be inserted further into the catheter hub 106 and into the catheter tube by advancing the needle 104 distally through and relative to the perimeter defining the opening 127 on the proximal wall until the proximal wall 126 is pressed against on the proximally facing surface thereof by the seating surface 125a of needle guard extension 125 on the needle hub. Roughly or approximately at about the same time, the elbow sections 94a, 94b are pushed distally to press against the internal projection 136. This juncture of the installation may be referred to as the pre-seated position of the needle guard.

From the pre-seated position of the needle guard, an additional insertion force at the needle hub 102 can cause the needle guard extension 125 to push against the proximal wall in the distal direction to force the elbow sections 94a, 94b against the projection 136 and causing the elbow sections 94a, 94b and the distal walls 90a, 90b to elastically bend radially inwardly towards the needle 104. With the elbow sections 94a, 94b displaced radially inwardly, the elbow section 94a, 94b of the arms 124a, 124b can now slide under and/or through the projection 136 in the distal direction.

Once the elbow sections 94a, 94b are clear of the projection 136 into the holding chamber 120b, the elbow sections 94a, 94b and the distal walls 90a, 90b can elastically spring back outwardly inside the holding chamber 120b and be in the seated position. With the distal walls 90a, 90b of the needle guard 122 inside the holding chamber 120b, the needle hub 102 can be inserted further until a physical stop is achieved between the catheter hub and the needle hub and the needle tip 110 extends distally of the distal opening 50 of the catheter tube. In the ready position, both the projection 136 and the needle guard extension 125 prevent the elbow sections 94a, 94b from moving proximally out of the holding chamber 120b.

For a given female Luer dimension of a catheter hub, a pre-determined space or clearance is available to incorporate various features inside the catheter hub. Thus, by utilizing a needle shaft with at least two diameter sections, such as the needle of FIG. 1B, a needle guard, such as those described elsewhere herein, can more readily be assembled into the catheter hub despite the needle having a relatively large needle diameter section for use with a relatively large catheter tube. For example, a catheter assembly comprising a needle shaft having a 14 gauge shaft diameter region 104a and an 18 gauge reduced diameter region 104b connected to one another by a transition region 104c can be use with a needle guard. The catheter tube can be sized for the 14 gauge needle section. This allows for a flow rate through the catheter tube that is greater than for a catheter tube sized for an 18 gauge needle. However, because of the 18 gauge reduced diameter region 104b at the proximal end of the needle shaft, the needle guard can be slidably positioned on the 18 gauge needle region and be seated inside the catheter hub with greater clearance compared to when the needle is made entirely from a 14 gauge needle. The different in diameters between an 18 gauge needle and a 14 gauge needle, as an example, allow other components inside the catheter hub, such as the needle guard, to utilize the extra space. Thus, at the pre-seated position, the elbow sections 94a, 94b of the needle guard are not biased outwardly as great when biased by the 18 gauge reduced diameter region of the needle shaft of the present disclosure and therefore the elbows or elbow sections do not have to deflect as much to slip through the projection 136 to be placed in the seated position compared to being biased by a 14 gauge needle. In the needle guard seated position, as shown in FIG. 1C, the undercut or maximum interior diameter of the catheter hub 106 where the elbows of the needle guard are located can also be reduced, due to the guard being biased by a relatively smaller needle diameter section of the shaft, to obtain more accuracy and shorter mold cycle times.

Another aspect of the present disclosure is understood to include a needle assembly comprising a catheter hub with a catheter tube and a needle hub with a needle. The needle can comprise at least two different diameter regions or sections connected to one another by a transition region. The catheter tube can be sized for the larger of the two diameters of the needle so as to be able to accommodate a greater infusion flow than if sized for only the smaller of the two diameter regions of the needle. Further, because the needle has a reduced diameter section, the reduced diameter does not bias the two arms of a needle guard radially outwardly the same amount compared to when the two arms are biased outwardly by the larger diameter region of the needle shaft. Thus, the needle guard can be seated inside the catheter hub without having to overly deflect or compress the two elbow sections of the needle guard through a projection inside the catheter hub to the same extent or amount compared to when the same needle guard is seated inside the same catheter hub but using a needle with a single diameter, and wherein said single diameter is the same as the larger of the two diameters of the present needle.

Following successful venipuncture, the needle hub 102 and the needle 104 can be separated from the catheter hub 106 by holding the catheter hub 106 and pulling the needle hub 102 proximally away from the catheter hub 106. As the needle 104 is pulled from the catheter hub 106 and the needle guard held by the internal projection 136, the reduced diameter region 104b slides relative to the curved lips 92a, 92b and in contact with the curved lips 92a, 92b. Then the transition region 104c and the shaft diameter region 104a of the needle slide relative to the curved lips 92a, 92b and in contact with the curved lips 92a, 92b as the needle continues its proximal retraction.

During retraction of the needle, the needle guard 122 may move proximally until it contacts the internal projection 136, if not already in contact with the internal projection. In one example, the elbow sections 94a, 94b approach the interior walls of the holding chamber 120b but do not contact the interior walls of the holding chamber 120b when the curved lips 92a, 92b are pressing against the side of the shaft diameter region 104a during the needle retraction. In another example, the elbow sections 94a, 94b contact the interior walls of the holding chamber 120b when the curved lips 92a, 92b press against the shaft diameter region 104a during the needle retraction.

The needle continues to move in the proximal direction until the needle tip 110 moves just proximal of the distal walls 90a 90b, or proximal of the two curved lips 92a, 92b, as shown and discussed below with reference to FIG. 1D. At about the same time or shortly thereafter, the change in profile 128 contacts the perimeter of the opening on the proximal wall of the needle guard 122.

Referring now to FIGS. 1C and 1D, the elbow sections of the needle guard 122 are located adjacent the projection 136 in the holding chamber 120b until the needle tip 110 moves just proximal of the two curved lips 92a, 92b. At this moment and no longer biased by the needle, the two arms 124a, 124b move radially inward primarily by established spring force created by selected spring steel material and specific bending prior to assembling onto needle shaft and the distal walls 90a, 90b cover the needle tip 110 in a protective position. With the needle tip 110 guarded by the needle guard 122 and the elbows moved radially inward and no longer engaging or impeded by the projection 136, the needle 104 can further retract proximally away from the catheter hub with the needle guard 122 covering the needle tip 110. The change in profile 128 engages the perimeter defining the opening 127 on the proximal wall 126 to pull the needle guard 122 proximally from the catheter hub 106 with the needle.

In other examples, the needle device 100 can incorporate a valve and a valve opener inside the catheter hub 106 for restricting flow in the proximal direction, such as for stopping blood flow coming out the open proximal end of the catheter hub following successful venipuncture. The valve and the valve opener can be similar to those disclosed in U.S. Pat. No. 9,149,625, the contents of which are expressly incorporated herein by reference.

Figure 2A:
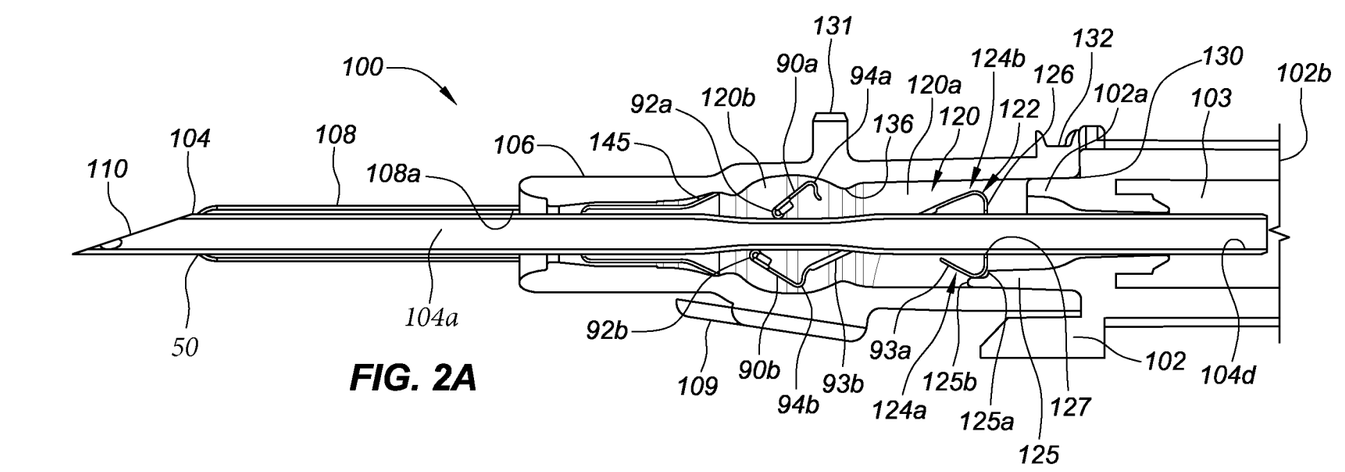
FIG. 2A is a cross-sectional side view of a needle device in accordance with further aspects of the present disclosure in the ready position.
Figure 2B:
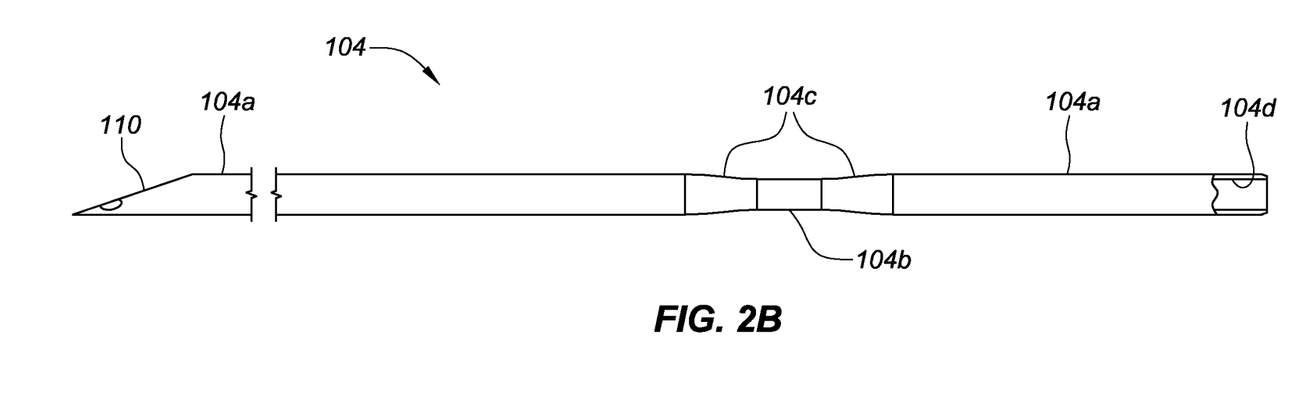
FIG. 2B is a side view of the needle of the needle device of FIG. 2A.

Turning now to FIGS. 2A and 2B, a cross-sectional side view of a needle device 100 and a side view of an alternative needle 104 provided in accordance with further aspects of the present disclosure are shown. The needle device 100 comprises a needle hub 102, a needle 104 extending distally of the needle hub 102, a catheter hub 106, a catheter tube 108 extending distally of a distal end of the catheter hub 106, and a needle guard 122 positioned in the catheter hub 106 in a ready position. The embodiment of the needle device 100 of FIG. 2A is similar to the needle device 100 of FIG. 1A except that the needle 104, as shown in FIG. 2B, has two transition regions 104c with the second transition region 104c enlarging the needle from a reduced diameter region 104b back up to a second shaft diameter region 104a proximally of the reduced diameter region 104b. The reduced diameter region 104b of the needle 104 of FIG. 2B extends a certain length before the second transition region 104c increases the shaft back to the shaft diameter region 104a. In an example, the length of the reduced diameter region 104b can be about 20% to about 90% of the length of the needle guard. In other examples, the length of the reduced diameter region 104b can be longer than the length of the needle guard, such as being 150% to 300% of the length of the needle guard. In other examples, a minimum limit can be set by the shape of the distal walls 90a, 90b of the needle guard.

Thus, an aspect of the present disclosure is understood to include a needle assembly comprising a catheter hub with a catheter tube and a needle hub with a needle. The needle can comprise at least two different diameter regions or sections and at least two transition sections or regions. In the present embodiment, the needle can comprise a shaft diameter region 104a, a transition region 104c that tapers from a large diameter to a smaller diameter in a proximal direction, a reduced diameter region 104b, and a transition region 104c that tapers from a small diameter to a larger diameter in the proximal direction, and a shaft diameter region 104a proximal of the second transition region 104c. The catheter tube can be sized for the larger of the two diameters of the needle so as to be able to accommodate a greater infusion flow than if sized for only the smaller of the two diameter regions of the needle. Further, because the needle has a reduced diameter section, the reduced diameter does not bias two arms of a needle guard radially outwardly the same amount compared to when the two arms are biased outwardly by the larger diameter region of the needle shaft, as discussed elsewhere herein. Thus, the needle guard can be seated inside the catheter hub without having to overly deflect or compress the two elbow sections of the needle guard through a projection inside the catheter hub to the same amount or extent compared to when the same needle guard is seated inside the same catheter hub but using a needle with a single diameter, and wherein said single diameter is the same as the larger of the two diameters of the present needle.

The two shaft diameter regions 104a of the present needle have substantially the same outer diameter, which is greater than the diameter of the reduced diameter region 104b. Specifically, as shown in FIG. 2B, the needle 104 has a shaft diameter region 104a that extends proximally from the needle tip 110 to a transition region 104c that tapers inwardly to a reduced diameter region 104b. The reduced diameter region 104b extends a certain distance to another transition region 104c, which tapers outwardly to another shaft diameter region 104a that extends to the needle hub 102. The more gradual the taper in the transition regions 104c, the less the frictional loss is through the bore 104d of the needle 104. In other examples, one or more of the transition regions 104c can comprise steps without a gradual taper. The reduction in the diameter of the bore 104d of the needle 104 at the transition region 104c and the reduced diameter region 104b does not decrease significantly as a result of forming the reduced diameter region 104b. Further, at least part of the shaft diameter region 104 adjacent the needle tip and the first transition region 104c are located inside the bore of the catheter tube proximal of the distal opening of the catheter tube.

As shown, the reduced diameter region 104b can be located along the length of the needle in an area where the two curved lips 92a, 92b or distal walls 90a, 90b, if no curved lips are incorporated, of the needle guard 122 contact the needle shaft, such as when in the ready to use position. Thus, as shown in FIG. 2A, the two curved lips 92a, 92b contact the reduced diameter region 104b, which is located between two transition regions 104c, in the ready position. Said differently, the reduced diameter region 104b comprises a short length extending along the length of the needle and is positioned adjacent the protrusion 136 or is centered in the holding chamber 102b in the ready position. The two curved lips 92a, 92b contact the reduced diameter region 104b, which is located, in an axial position, adjacent the internal projection 136. The localized region of the reduced diameter region 104b can be produced by mechanical swaging or controlled squeezing of a drawn cannula, the localized region being selected to be where the distal walls 90a, 90b or curved lips 92a, 92b press against the reduced diameter region 104b in the ready position. Said differently, the localized region is at or near the projection 136 in the ready position and the distal walls 90a, 90b or curved lips 92a, 92b of the needle guard press thereagainst. Because the reduced diameter region 104a of the needle 104 of FIG. 2B extends only a short distance instead of extending to the proximal end of the needle 104, as shown with reference to the needle 104 of FIG. 1B, mechanical swaging, forging, or controlled squeezing to form the reduced diameter region 104a is limited to a relatively shorter length of the needle than for the needle of FIG. 1B.

When assembling the needle device 100 of FIG. 2A, the needle guard 122 can be slidably positioned on the needle 104 proximal of the needle tip 110 with the proximal wall 126 contacting the needle guard extension 125 or positioned distal of the needle guard extension 125, such as being spaced from the needle guard extension 125. With the needle guard 122 positioned on the needle 104 and the needle attached to the catheter hub, the needle 104 can then be inserted into the catheter hub 106 until the catheter hub physically stops the needle hub.

As described above for assembling the needle device 100 of FIG. 1A, during insertion of the needle 104, the elbow sections 94a, 94b of the needle guard will advance distally against a proximal side of the projection 136, which hinders or limits the needle guard 122 from moving further distally into the holding chamber 120b. At this point, the needle 104 can be further inserted into the catheter hub 106 by sliding the needle 104 through the opening 127 on the proximal wall 126 of the needle guard 122 until the needle guard extension 125 of the needle hub abuts the proximal wall 126. At this point of the assembly, as discussed above with reference to the needle assembly of FIG. 1A, the two curved lips 92a, 92b or distal walls 90a, 90b are biased outwardly by the reduced diameter region 104b.

With the needle guard extension 125 pressing against the proximal wall 126 in the distal direction, an additional force applied to the needle hub 102 pushes the elbow sections 94a, 94b against the projection 136 and causes the elbow sections 94a, 94b and the distal walls 90a, 90b to elastically bend inwardly against the reduced diameter region 104b of the needle. The elbow sections 94a, 94b, being reduced in cross-sectional dimension by the deformation, can now slide through the internal projection 136 and then elastically spring back outwardly once the elbow sections 94a, 94b are inside the holding chamber 120b. By utilizing a relatively smaller diameter section to bias the arms during installation, more space or room is available for the needle guard so that the elbow sections are not deflected to the same amount or extent compared to a single diameter shaft and wherein the single diameter shaft has the same size as the larger of the two diameter sections of the present device.

With the distal walls 90a, 90b of the needle guard 122 inside the holding chamber 120b, the needle hub 102 can be inserted further until physically stopped by the catheter hub 106 in the ready position. In the ready position, both the projection 136 and the needle guard extension 125 prevent the elbow sections 94a, 94b from moving proximally out of the holding chamber 120b. Following successful venipuncture, the needle 104 can be pulled from the catheter hub 106 with the needle tip 110 secured by the needle guard 122 in the protective position, as described above with reference to the needle device of FIG. 1D.

Thus, an aspect of the present disclosure is a catheter assembly comprising a catheter tube positioned around or over a needle shaft and wherein the needle shaft has at least two different shaft diameters and wherein the bore of the catheter tube is sized and shaped to fit over the larger of the two diameters. The bore of the catheter tube can also be sized and shaped to fit over both diameter regions of the needle shaft. The distal end 50 of the catheter tube 108 can neck or taper down to form a seal with the larger of the two diameters 104a near the needle tip 110. Further, because the transition region 104c and the needle shaft with the smaller of the two diameters, such as the reduced diameter region 104b, are located inside the bore of the catheter tube, the present needle assembly has at least two different annular spaces. For example, the annular space between the needle and the catheter tube at the shaft diameter region 104a, proximal of the tapered distal end 50, will be smaller or narrower than the annular space between the needle and the catheter tube at the reduced diameter region 104b.

An aspect of the present disclosure is further understood to include a variable annular space region at the transition region 104c of the needle shaft. For example, as the transition region 104c tapers from the shaft diameter region 104a to the reduced diameter region 104b, the annular space at the transition region 104c is variable at least along part of the length of the transition region 104c. Still further, since the present needle has a second transition region 104c and a separate shaft diameter region 104a proximal of the second transition region 104c, the present needle device has additional annular spaces, namely a variable annular space region at the second transition region 104c and a second smaller annular space at the second shaft diameter region 104a proximal of the second transition region.

Figure 3A:
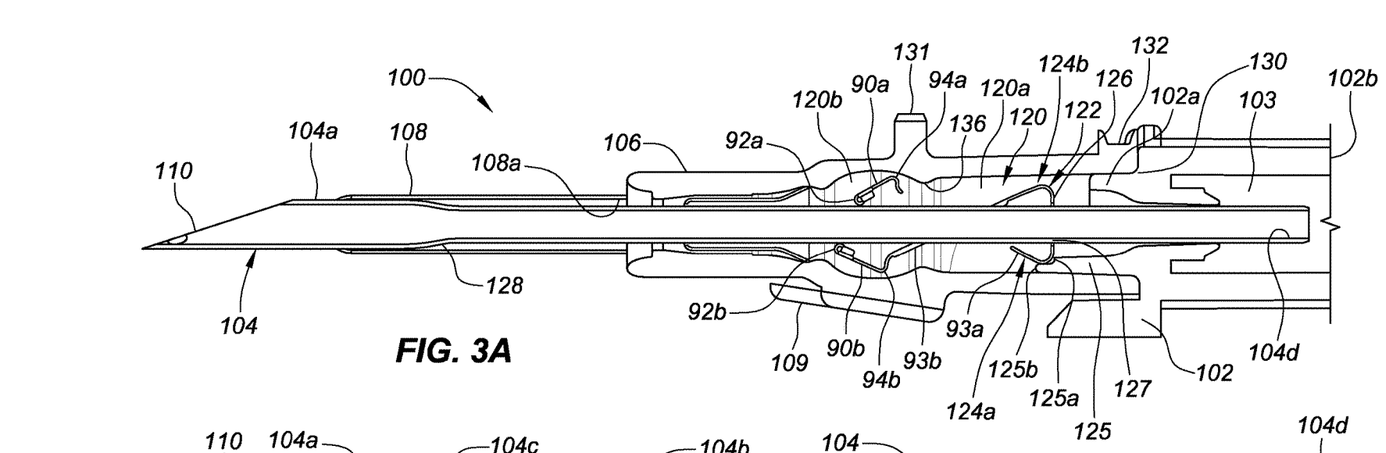
FIG. 3A is a cross-sectional side view of a needle device in accordance with yet further aspects of the present disclosure in the ready position.
Figure 3B:
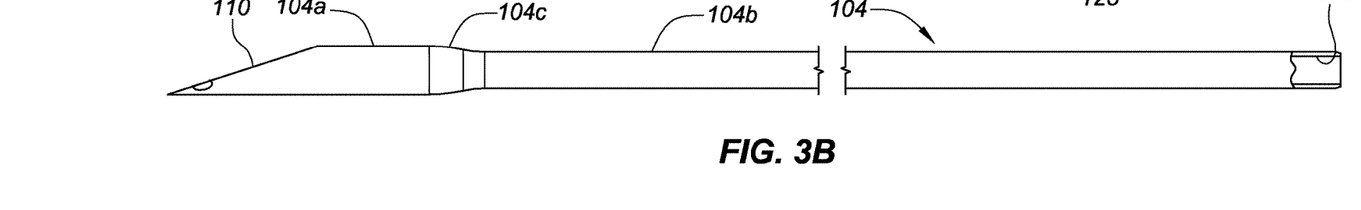
FIG. 3B is a side view of the needle of the needle device of FIG. 3A.

Turning now to FIGS. 3A and 3B, a cross-sectional side view of a needle device 100 and a side view of an alternative needle 104 provided in accordance with further aspects of the present disclosure are shown. The needle device 100 comprises a needle hub 102, a needle 104 extending distally of the needle hub 102, a catheter hub 106, a catheter tube 108 extending distally of a distal end of the catheter hub 106, and a needle guard 122 positioned in the catheter hub 106 in a ready position.

The embodiment of the needle device 100 of FIG. 3A is similar to the needle device 100 of FIG. 1A, except that a transition region 104c of the needle 104 between a shaft diameter region 104a of the needle 104 and a reduced diameter region 104b of the needle 104 extends closer to the needle tip 110 compared transition region and the shaft diameter region of the needle of FIG. 1B.

Figure 3C:
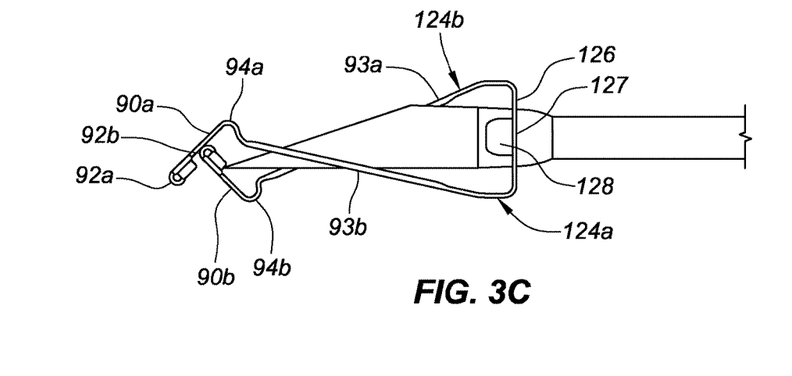
FIG. 3C is a close-up side view of the needle secured by the needle guard in the protective position.

In an example, the needle 104, as shown in FIG. 3B, has a shaft diameter region 104a transitioning to a reduced diameter region 104b just proximal of the tapered distal end opening 50 of catheter tube, which forms a seal with the shaft diameter region 104a. Furthermore, the shaft diameter region 104a itself together with the transition region 104c may act as a change in profile 128 for engaging a perimeter of the opening on the proximal wall of the needle guard. Alternatively, a change in profile 128 can be formed on the transition region 104c, as shown in FIG. 3C and discussed below. The reduced diameter region 104b can be produced by mechanical swaging or controlled squeezing of a drawn cannula before or after grinding.

With reference again to FIG. 3A and similar to the embodiment of FIG. 1A, part of the shaft diameter region 104a and the transition region 104c are located inside the bore of the catheter tube, proximal of the distal opening 50, in the ready position. The catheter tube is therefore selected to fit around the larger diameter region of the needle while the reduced diameter region at the proximal end of the shaft facilitates assembly of a needle guard into to catheter hub, as previously discussed with reference to the needle assembly of FIG. 1A.

When assembling the needle device 100 of FIG. 3A, the needle guard 122 is slidably positioned on the needle 104 proximal of the needle tip 110 with the proximal wall 126 contacting the needle guard extension 125 or positioned distal of the needle guard extension 125, such as being spaced therefrom. The two curved lips 92a, 92b or distal walls 90a, 90b, if the curved lips are not incorporated, are biased against the reduced diameter region 104b. With the needle guard 122 positioned on the reduced diameter region 104b and the needle attached to the needle hub, the needle 104 can be inserted distally into the catheter hub 106.

As described for assembling the needle device 100 of FIG. 1A above, during insertion of the needle 104, the elbow sections 94a, 94b are advanced distally against the projection 136, which hinders the needle guard 122 from moving further distally into the holding chamber 120b. However, the needle can still advance distally by moving relative to the needle guard and sliding through the opening 127 of the proximal wall 126 of the needle guard 122 until the needle guard extension 125 abuts the proximal wall 126. With the needle guard extension 125 pressing against the proximal wall 126, an additional distally directed force can be applied to the needle hub 102 to push the elbow sections 94a, 94b against the projection 136 to elastically bend the needle guard and compress the elbows radially. The elbow sections 94a, 94b, now reduced in cross-sectional dimension, slide past the projection 136 and elastically spring back outwardly once inside the holding chamber 120b. The needle hub 102 can be advanced until physically stopped by the catheter hub 106 in the ready position. In the ready position, both the projection 136 and the needle guard extension 125 prevent the elbow sections 94a, 94b from moving proximally out of the holding chamber 120b and the needle tip extends distally of the distal opening 50 of the catheter tube. By utilizing a relatively smaller diameter section to bias the arms during installation, more space or room is available for the needle guard so that the elbow sections are not deflected to the same amount or extent compared to a single diameter shaft and wherein the single diameter shaft has the same size as the larger of the two diameter sections of the present device.

Turning now to FIG. 3C, a side view of another embodiment of a needle 104 and the needle guard 122, discussed elsewhere herein, are shown in the protective position with the needle tip 110 covered by the two distal walls 90a, 90b, such as following successful venipuncture and the needle is retracted from the needle hub. As shown, the curved lips 92a, 92b of the needle guard 122 are no longer biased against the needle 104. The change in profile 128 on the needle 104 is shown abutting the proximal wall 126, and more specifically, the perimeter defining the opening 127 on the proximal wall 126 to prevent the needle guard 122 from displacing distally off of the needle tip 110 after the needle tip 110 has been safely guarded in the protective position. The change in profile 128 is located on the transition region 104c, as shown in FIG. 3C. However, the change in profile 128 may be located on the shaft diameter region 104a or the reduced diameter region 104b. Alternatively, as discussed above, for FIGS. 3A and 3B, the shaft diameter region 104a itself may function as the change in profile 128. In the protective position, the two curved lips 92a, 92b or distal walls 90a, 90b prevent the needle tip 110 from moving distal the needle guard 122, and the engagement between the change in profile 128 and the opening 127 prevent the needle guard 122 from being removed from the needle 104.

Methods of making and of using the needle devices shown and described elsewhere herein are within the scope of the present disclosure.

Although limited embodiments of the needle devices and their components have been specifically described and illustrated herein, many modifications and variations will be apparent to those skilled in the art. Furthermore, it is understood and contemplated that features specifically discussed for one needle device embodiment may be adopted for inclusion with another needle device embodiment, provided the functions are compatible. For example, various features disclosed for the embodiment of FIGS. 1A-1D may be incorporated with the embodiments of FIGS. 2A-3C provided the functions do not conflict. Accordingly, it is to be understood that the needle devices and their components constructed according to principles of the disclosed device, system, and method may be embodied other than as specifically described herein. The disclosure is also defined in the following claims.

What is claimed is:

1. A needle device comprising:
   a catheter hub having a body with an interior surface defining an interior cavity and having a proximal opening;
   a catheter tube extending distally of the catheter hub and comprising a bore and a distal opening;
   a needle hub;
   a needle extending distally of the needle hub;
      said needle comprising a shaft and a needle tip having an edge defining a needle opening extending distally of the distal opening of the catheter tube in a ready to use position;
      said needle having a shaft diameter region and a reduced diameter region connected to one another by a transition region;
         wherein an outer diameter of the needle at the shaft diameter region is larger than an outer diameter of the needle at the reduced diameter region;
         wherein at least part of the shaft diameter region and the transition region are located in the bore of the catheter tube, proximal of the distal opening; and
         wherein the shaft diameter region extends up to the needle tip; and
   a needle guard located in the interior cavity of the catheter hub, said needle guard comprising a proximal wall and at least one arm extending distal of the proximal wall, said at least one arm comprising an elbow section located between a distal wall and an elongated arm portion of the at least one arm;
      wherein the elbow section is spaced from the interior surface of the catheter hub in the ready to use position;
      wherein the distal wall presses against the reduced diameter region and the elbow section is located distal of an annular projection in the interior cavity of the catheter hub in the ready to use position; and
      wherein the reduced diameter region of the shaft does not bias the distal wall to bias the elbow section of the needle guard radially outward in the ready to use position a same amount compared to when the distal wall is biased outward by the shaft diameter region of the shaft.

2. The needle device of claim 1, wherein the at least one arm is a first arm and the needle guard comprises a second arm, and wherein the first arm and the second arm press against the reduced diameter region in the ready to use position.

3. The needle device of claim 2, wherein the second arm comprises a distal wall and an elbow section and the elbow section is located is located distal of the reduced diameter region in the ready to use position.

4. The needle device of claim 3, wherein the reduced diameter region extends from the needle hub to at least a distal end of the catheter hub in the ready to use position.

5. The needle device of claim 3, wherein the needle further comprises a shaft diameter region proximal of the reduced diameter region.

6. The needle device of claim 5, wherein the needle further comprises a change in profile proximal of the needle tip, wherein the change in profile is larger than a perimeter defining an opening on the proximal wall.

7. The needle device of claim 3, wherein the reduced diameter region extends from the needle hub to adjacent the needle tip in the ready to use position.

8. The needle device of claim 7, wherein the shaft diameter region is larger than a perimeter defining an opening on the proximal wall.

9. The needle device of claim 1, wherein the transition region has a length and a taper to allow the distal wall of the needle guard to slide relative to the transition region when the needle hub is pulled in a proximal direction to remove the needle from the catheter tube.

10. The needle device of claim 1;
   wherein the needle further comprises a change in profile proximal of the needle tip;
   wherein the change in profile is larger than a perimeter defining an opening on the proximal wall; and
   wherein the opening on the proximal wall is sized to allow the reduced diameter region to pass through the opening and not allow the change in profile to pass through the opening.

11. The needle device of claim 1, wherein a length of the reduced diameter region is about 20% to about 90% of a length of the needle guard.

12. The needle device of claim 1, wherein a recessed length of the shaft diameter region of the needle located proximally of the distal opening of the catheter tube is about 50% to about 80% of a total length of the shaft of the needle.

13. The needle device of claim 12, wherein the recessed length of the shaft diameter region of the needle is at least 0.1 times a distal length of the shaft diameter region located distally of the distal opening of the catheter tube.

14. A method for manufacturing a needle device, the method comprising:

attaching a catheter tube to a catheter hub, said catheter hub comprising a hub body comprising an exterior surface and an interior surface defining an interior cavity;

projecting a needle through an entire length of the catheter tube so that a needle tip of the needle, which has an edge defining a needle opening, extends distally of a distal end of the catheter tube in a ready to use position;

said needle having a proximal end attached to a needle hub and a shaft having a shaft diameter region, a reduced diameter region, and a transition region between the shaft diameter region and the reduced diameter region;

wherein a length of the shaft diameter region and a length of the reduced diameter region are both longer than a length of the transition region;

wherein the shaft diameter region has an outside diameter that is larger than an outside diameter of the reduced diameter region; and wherein at least part of the shaft diameter region and the transition region are located in a bore of the catheter tube proximal of the distal end of the catheter tube in the ready to use position;

providing a needle guard in the interior cavity of the catheter hub, the needle guard comprising a proximal wall and two arms extending distally of the proximal wall; and pressing the two arms of the needle guard against the reduced diameter in the ready to use position;

wherein an elbow section of at least one of the two arms is spaced from the interior surface of the catheter hub in the ready to use position;

wherein the reduced diameter region of the shaft does not bias the two arms of the needle guard radially outward a same amount compared to when the two arms are biased outward by the shaft diameter region of the shaft; and wherein the transition region has a length and a taper.

15. The method of claim 14, further comprising:
pulling the reduced diameter region of the needle through an opening in the proximal wall of the needle guard to engage a change in profile of the needle against a perimeter that defines the opening.

16. The method of claim 15, further comprising locating an elbow section of at least one of the two arms distal of a projection inside the interior cavity of the catheter hub in the ready to use position.

17. The method of claim 16, wherein a curved lip extending from a distal wall of each arm presses against the reduced diameter region in the ready to use position.

18. The method of claim 16, wherein the reduced diameter region extends from the needle hub through the opening of the proximal wall to at least a distal end of the catheter hub in the ready to use position.

19. The method of claim 18, wherein the needle further comprises a change in profile proximal of the needle tip, wherein the change in profile is larger than the perimeter defining the opening on the proximal wall.

20. The method of claim 16, wherein the reduced diameter region is centered about two distal walls of the needle guard in the ready to use position and the transition region is located on opposite sides of the reduced diameter region.

21. The method of claim 20, wherein the needle further comprises a change in profile adjacent the needle tip, wherein the change in profile is larger than the perimeter defining the opening on the proximal wall.

22. The method of claim 16, wherein the reduced diameter region extends from the needle hub to adjacent the needle tip in the ready to use position.

23. The method of claim 22, wherein the shaft diameter region is larger than a perimeter defining an opening on the proximal wall.

24. A needle device comprising:
a catheter hub having a body with an interior surface and a catheter tube attached at a distal end of the body;
a needle comprising:
a proximal end attached to a needle hub;
a needle tip at a distal end with an edge defining a needle opening;
a shaft diameter region, a transition region, and a reduced diameter region;
wherein the reduced diameter region is located proximally of the needle tip and proximally of the shaft diameter region;
wherein the shaft diameter region has a larger outside diameter dimension than an outside diameter dimension of the reduced diameter region;
wherein the shaft diameter region has a length that extends up to the needle tip; and
wherein a portion of the shaft diameter region is located within a bore of the catheter tube in a ready to use position; and
a change in profile located proximally of the needle tip; and
a needle guard comprising:
a proximal wall having a proximally facing wall surface and a distally facing wall surface; and
two arms extending distally of the distally facing wall surface with each arm comprising an elbow;
wherein the interior cavity of the catheter hub has a holding chamber comprising a first interior section with a first internal diameter located distally of an second interior section with a second internal diameter, which is larger in diameter than the first internal diameter and the two elbows of the needle guard are located inside the interior cavity and distal of the first and second interior sections while the two arms press against the reduced diameter region of the needle in the ready to use position;
wherein a guard diameter defined by the two elbows is smaller in dimension then the second internal diameter; and
wherein the reduced diameter region of the shaft does not bias the two arms of the needle guard radially outward a same amount compared to when the two arms are biased outward by the shaft diameter region of the shaft.

25. The needle device of claim 24, wherein the change in profile is located at the shaft diameter region.

26. The needle device of claim 25, wherein the change in profile is located distal of the transition region.

27. The needle device of claim 24, wherein the catheter hub comprises a reduced diameter region and wherein an elbow section on each of the two arms is located distal of the reduced diameter region of the catheter hub.

* * * * *